(12) United States Patent
Mahajan et al.

(10) Patent No.: US 8,003,602 B2
(45) Date of Patent: Aug. 23, 2011

(54) ANTIBACTERIAL COMPOUNDS

(75) Inventors: Girish Badrinath Mahajan, Mumbai (IN); Saji David George, Mumbai (IN); Prafull Vasant Ranadive, Mumbai (IN); Prabhu Dutt Satyanarayan Mishra, Mumbai (IN); Sreekumar Sankaranarayanan Eyyammadichiyil, Mumbai (IN); Rajan Mukund Panshikar, Mumbai (IN); Satish Namdeo Sawant, Mumbai (IN); Sridevi Krishna, Mumbai (IN); Meenakshi Sivakumar, Mumbai (IN); Koteppa Pari, Mumbai (IN); Becky Mary Thomas, Mumbai (IN); Zarine Eruch Patel, Mumbai (IN); Ram Vishwakarma, Mumbai (IN); Chandrakant Govind Naik, Dona Paula (IN); Lisette D'Souza, Dona Paula (IN); Prabha Devi, Dona Paula (IN)

(73) Assignees: Piramal Life Sciences Limited, Mumbai (IN); Council of Scientific and Industrial Research, New Delhi (IN)

( * ) Notice: Subject to any disclaimer, the term of this patent is extended or adjusted under 35 U.S.C. 154(b) by 435 days.

(21) Appl. No.: 12/226,403

(22) PCT Filed: Apr. 10, 2007

(86) PCT No.: PCT/IB2007/051268
§ 371 (c)(1),
(2), (4) Date: Oct. 17, 2008

(87) PCT Pub. No.: WO2007/119201
PCT Pub. Date: Oct. 25, 2007

(65) Prior Publication Data
US 2009/0076094 A1    Mar. 19, 2009

Related U.S. Application Data

(60) Provisional application No. 60/809,674, filed on May 31, 2006.

(30) Foreign Application Priority Data

Apr. 18, 2006   (IN) ............................ 607/MUM/2006

(51) Int. Cl.
   *A61K 38/12*   (2006.01)
(52) U.S. Cl. ........... 514/2.4; 514/2.6; 514/2.7; 514/21.1
(58) Field of Classification Search .................. None
   See application file for complete search history.

(56) References Cited

U.S. PATENT DOCUMENTS
7,022,667 B2   4/2006   Hudyma et al.

OTHER PUBLICATIONS

Cohen, M. "Antimicrobial resistance: prognosis for public health", Trends in Microbiology, vol. 2, No. 10, Oct. 1994, pp. 422-425.

(Continued)

*Primary Examiner* — Christina Bradley
(74) *Attorney, Agent, or Firm* — Hamre, Schumann, Mueller & Larson, P.C.

(57) ABSTRACT

This invention relates to a novel purified compound PM181104, of formula:

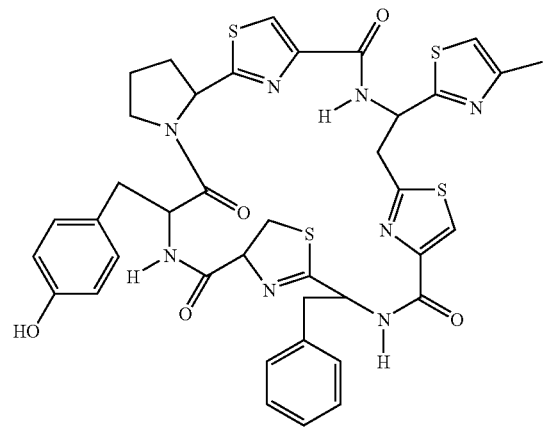

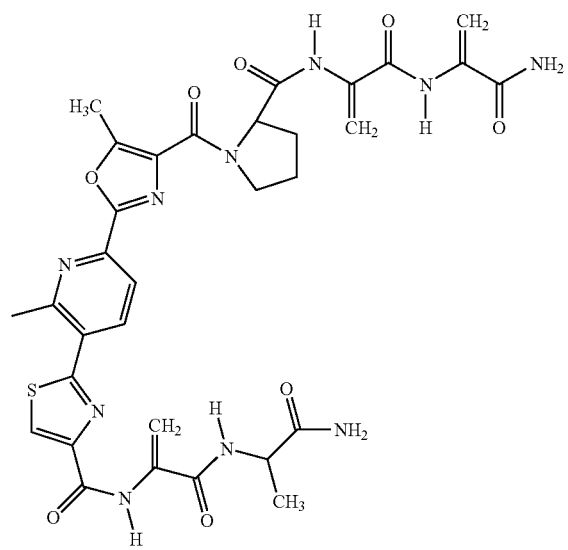

of molecular weight 1514 and molecular formula $C_{69}H_{66}N_{18}O_{13}S_5$; which is obtained by fermentation of the microorganism belonging to *Kocuria* species (ZMA B-1/MTCC 5269). The invention includes all stereoisomeric forms and all tautomeric forms of the compound PM181104 and pharmaceutically acceptable salts and derivatives such as esters and ethers. The present invention further relates to processes for the production of the novel antibacterial compound(s), to the production of the microorganism belonging to *Kocuria* species (ZMA B-1/MTCC 5269), and to pharmaceutical compositions containing the novel compound(s) as an active ingredient and its/their use in medicines for treatment and prevention of diseases caused by bacterial infections.

21 Claims, 4 Drawing Sheets

OTHER PUBLICATIONS

Aeschlimann, J. et al. "Pharmacodynamic Analysis of the Activity of Quinupristin-Dalfopristin against Vancomycin-Resistant *Enterococcus faecium* with Differing MBCs via Time-Kill-Curve and Postantibiotic Effect Methods", Antimicrobial Agents and Chemotherapy, vo. 42, Sep. 1998, pp. 2188-2192.

Livermore, D. "Bacterial Resistance: Origins, Epidemiology, and Impact", Bacterial Resistance-CID, Supplement I, vol. 36, 2003, S11-S23.

Mutnick, A. et al., "Linezolid Resistance Since 2001: SENTRY Antimicrobial Surveillance Program", The Annals of Pharmacotherapy, vol. 37, Jun. 2003, pp. 769-774.

Canu, A. et al. "Overcoming Bacterial Resistance by Dual Target Inhibition: The Case of Streptogramins", Current Drug Targets-Infectious Disorders, vol. I, 2001, pp. 215-225.

Mathew, A. et al. "Synthesis and Evaluation of Some Water-Soluble Prodrugs and Derivatives of Taxol with Antitumor Activity", J. Med Chem, vol. 35, 1992, pp. 145-151.

Saulnier, Mark et al. "Synthesis of Etoposide Phosphate, BMY-40481: A Water-Soluble Clinically Active Prodrug of Etoposide", Bioorganic & Medicinal Chemistry Letters, vol. 4, No. 21, 1994, pp. 2567-2572.

Von Hunolstein, C. et al. "Penicillin tolerance amongst non-toxigenic *Corynebacterium diphtheriae* isolated from cases of pharyngitis", Journal of Antimicrobial Chemotherapy, vol. 50, 2002, pp. 125-128.

Baltz, R. et al. "Natural Products to drugs: daptomycin and related lipopeptide antibiotics", Natural Product Report, vol. 22, Dec. 2005, pp. 717-741.

March, J., "Advanced Organic Chemistry". 1992, 4$^{th}$ Edition, pp. 393-398.

March, J., "Ethers", pp. 389-390 and 654-655.

ANTIBACTERIAL COMPOUNDS

FIELD OF THE INVENTION

This invention relates to a novel compound PM181104, having antibacterial activity, which is obtained by fermentation of the microorganism belonging to *Kocuria* species (ZMA B-1/MTCC 5269). The invention also includes all stereoisomeric forms and all tautomeric forms of PM181104 and pharmaceutically acceptable salts and derivatives thereof. The present invention further relates to processes for the production of the novel antibacterial compound(s), to the production of the microorganism belonging to *Kocuria* species (ZMA B-1/MTCC 5269), and to pharmaceutical compositions containing the novel compound(s) as an active ingredient and its/their use in medicines for treatment and prevention of diseases caused by bacterial infections.

BACKGROUND OF THE INVENTION

The surfacing of bacterial resistance to a number of antimicrobial agents such as beta-lactam antibiotics, macrolides, quinolones, and vancomycin is becoming a major health problem worldwide (Trends In Microbiology, 1994, 2, 422-425). The most significant problem in clinical practice is the increase in incidence of methicillin-resistant *Staphylococcus aureus* (MRSA) infections. At present, the only effective treatment for multiple resistant MRSA infections is vancomycin. However, there are a number of reports of emerging vancomycin resistance in some MRSA isolates (Antimicrobial Agents and Chemotherapy, 1998, 42, 2188-2192). Another group of clinically relevant multiple drug resistant bacteria that has emerged recently is Enterococci, some of which also exhibit vancbmycin resistance. The appearance of vancomycin resistant Enterococci (VRE) infections has forced a dilemma upon physicians. Combinations of Linezolid, an oxazolidinone compound, and streptogramin are the new drugs of choice for treating MRSA infections. However, resistance to these oxazolidinone (Clinical Infectious Diseases, 2003, 36, supplement 1, S11-S23; Annals of Pharmacotherapy, 2003, 37, 769-74) streptogramin combinations (Current Drug Targets Infectious Disorders, 2001, 1, 215-25) and various glycopeptides (Clinical Infectious Diseases, 2003, 36, supplement 1, S11-S23) require expanded development of agents with alternative targets or modes of action. The mounting resistance of the important community acquired pathogen *Streptococcus pneumoniae* to penicillin and other antibacterials is also becoming a global health problem. Multi drug-resistant strains of *Mycobacterium tuberculosis* have surfaced in several countries. The emergence and spread of resistant nosocomial and community-acquired pathogens is becoming a great menace to global public health.

There is an urgent need to discover new compounds, which can be used as drugs to treat patients infected with bacteria, particularly the multi drug resistant bacteria such as MRSA and VRE.

SUMMARY OF THE INVENTION

The present invention relates to a novel purified compound, (designated herein as PM181104), isolated from the fermented broth of the microorganism belonging to *Kocuria* species (ZMA B-1/MTCC 5269), having antibacterial activity.

The invention also relates to all stereoisomeric forms and all tautomeric forms of PM181104 and pharmaceutically acceptable salt(s) and ester and ether derivative(s) thereof, represented by formula I (as herein described).

The compound PM181104, and isomers, pharmaceutically acceptable salt(s) and ester and ether derivative(s) thereof, are useful for the treatment and prevention of diseases caused by bacteria, particularly the multi drug resistant bacteria such as MRSA and VRE.

The invention further relates to pharmaceutical compositions comprising the novel compound PM181104, an isomer, a pharmaceutically acceptable salt(s), an ester or an ether derivative thereof, as an active ingredient for the treatment of medical conditions caused by bacteria, particularly the multi drug resistant bacteria such as MRSA and VRE.

The present invention further relates to processes for the production of the compound PM181104 and/or its isomer(s) from the microorganism belonging to *Kocuria* species (ZMA B-1/MTCC 5269).

The present invention also relates to processes for the production of microorganism belonging to *Kocuria* species (ZMA B-1/MTCC 5269), which on cultivation produces the compound PM181104 and its isomers.

The present invention also relates to processes for the production of the ester and ether derivatives of the compound PM181104.

DETAILED DESCRIPTION OF THE INVENTION

The present invention provides a novel antibacterial compound PM181104 and also includes all stereoisomeric forms and all tautomeric forms of PM181104 and pharmaceutically acceptable salts and derivatives, such as esters and ethers thereof.

Accordingly, the present invention relates to novel antibacterial compounds of the following formula I;

Formula I wherein R=H (PM181104), alkyl, alkylcarbonyl, (HO)$_2$PO—, alkyl-OPO(OH)—, (alkyl-O)$_2$PO—, cycloalkyl, cycloalkylcarbonyl, aryl, arylcarbonyl, heterocyclyl and heterocyclyl carbonyl.

As used herein, the term "alkyl" whether used alone or as part of a substituent group, refers to the radical of saturated aliphatic groups, including straight or branched-chain alkyl groups. Furthermore, unless stated otherwise, the term "alkyl" includes unsubstituted alkyl groups as well as alkyl groups, which are substituted by one or more different substituents. In preferred embodiments, a straight chain or branched chain alkyl has 20 or fewer carbon atoms in its backbone (e.g., $C_1$-$C_{20}$ for straight chain, $C_3$-$C_{20}$ for branched chain). Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, heptadecyl and eicosyl, the n-isomers of all these residues; isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or tert-butyl. A substituted alkyl refers to an alkyl residue in which one or more, hydrogen atom, for example, 1, 2, 3, 4 or 5 hydrogen atoms are replaced with substituents, for example, halogen, hydroxyl, sulphonyl, alkoxyl, cycloalkyl, cyano, azido, amino, acyloxy, heterocyclo, aralkyl, aryl or fluorescent groups such as NBD [N-(7-nitrobenz-2-oxa-1,3-diazol-4-yl)amino] or BODIPY [4,4-difluoro-5,7-dimethyl-4-bora-3a,4a-diaza-s-indacene group.

As used herein, the term "cycloalkyl" refers to a saturated mono- or bicyclic ring system containing 3-10 carbon atoms, and more preferably having 3, 4, 5, 6 or 7 carbon atoms in the ring structure. Examples of cycloalkyl residues containing 3, 4, 5, 6 or 7 ring carbon atoms are cyclopropyl, cyclobutyl, cyclopentyl, cyclohexyl or cycloheptyl. Furthermore, unless stated otherwise, the term 'cycloalkyl' includes unsubstituted cycloalkyl and cycloalkyl which is substituted by one or more identical or different groups selected from halogen, hydroxyl, alkoxyl, alkyl, cycloalkyl, cyano, amino, aminoalkyl, acyloxy, heterocyclo, aralkyl, and/or an aryl group.

As used herein, the term "aryl" refers to a monocyclic or polycyclic hydrocarbon group having up to 10 ring carbon atoms, in which at least one carbocyclic ring is present that has a conjugated π electron system. Suitable examples of $C_6$-$C_{10}$-aryl residues include phenyl, naphthyl or biphenyl, especially phenyl and naphthyl. Aryl residues, for example phenyl or naphthyl, can in general be optionally substituted by one or more substituents, up to five identical or different substituents selected from the groups consisting of halogen, alkyl, hydroxyl, acyloxy, amino, substituted amino, cyano.

The term "heterocyclyl" refers to a saturated, partially unsaturated or aromatic monocyclic or polycyclic heterocyclic ring system containing 5, 6, 7, 8, 9 or 10 ring atoms of which 1, 2 or 3 are identical or different heteroatoms selected from: nitrogen, oxygen and sulfur. Suitable examples of such heterocyclyl groups are pyridinyl, piperazinyl, piperidinyl, imidazolyl, pyrrolidinyl and morpholinyl. In polycyclic heterocyclic ring system the heterocyclyl may comprise either fused rings in which two or more carbons are common to two adjoining rings, or bridged rings in which rings are joined through non-adjacent atoms. In polycyclic heterocyclic ring system the heterocyclyl preferably comprises two fused rings (bicyclic), at least one of which is a 5- or 6-membered heterocyclic ring. Exemplary bicyclic heterocyclic groups include benzoxazolyl, quinolyl, isoquinolyl, carbazolyl, indolyl, isoindolyl, phenoxazinyl, benzothiazolyl, benzimidazolyl, benzoxadiazolyl and benzofurazanyl. Heterocyclyl residues, can in general be optionally substituted by one or more identical or different substituents selected from the groups consisting of halogen, alkyl, hydroxyl, acyloxy, amino, substituted amino, cyano.

According to a preferred embodiment of the present invention, the group R in the formula I may represent According to a more preferred embodiment, the novel compound PM181104 represented by the above formula I (wherein R=H) is isolated from the fermented broth of the microorganism belonging to *Kocuria* species (ZMA B-1/MTCC. 5269) and is further purified.

The novel compound PM181104 has the molecular formula $C_{69}H_{66}N_{18}O_{13}S_5$ (molecular weight 1514) and may be characterised by any one or more of its physico-chemical and spectral properties, such as high performance liquid chromatography (HPLC), mass spectrum (MS), ultra violet (UV), infra red (IR) and nuclear magnetic resonance (NMR) spectroscopic data as discussed herein below.

The structure of the novel compound PM181104 has been elucidated and its complete characterization is done by HPLC, MS, UV, IR and NMR spectroscopic data. The structure was confirmed by the three-dimensional (3D) NMR study of bioactive $^{15}N$ and $^{13}C$-labeled PM181104.

The compound PM181104 and its ester and ether derivatives are new antibiotics active against bacteria, particularly the multi drug resistant bacteria such as MRSA and VRE.

The microorganism, which may be used for the production of the compound PM181104, is a strain of *Kocuria* species (ZMA B-1/MTCC 5269), herein after referred to as culture no. ZMA B-1, isolated from a marine sample collected in Palk Bay, Tamil Nadu coast, India.

The present invention further provides a process for the production of the compound PM181104 from culture no. ZMA B-1, its mutants and variants, comprising the steps of: growing the culture no. ZMA B-1 under submerged aerobic conditions in a nutrient medium containing one or more sources of carbon and one or more sources of nitrogen and optionally nutrient inorganic salts and/or trace elements; isolating the compound PM181104 from the culture broth; and purifying the compound PM181104 using purification procedures generally used in the related art.

As used herein, the term "mutant" refers to an organism or cell carrying a mutation, which is an alternative phenotype to the wild-type.

As used herein, the term "variant" refers to an individual organism that is recognizably different from an arbitrary standard type in that species.

Preliminary identification of culture no. ZMA B-1, which is the producer of PM181104 was performed by examination of its colony morphology, wet mount observations and Gram stain reaction. Microscopic studies on the strain of isolated culture no ZMA B-1 were carried out on Zobell Marine Broth 2216 (marine broth 2216), containing 1.5% agar and observations were made at 1, 2 and 3 days of incubation at 25° C.

Growth on Zobell Marine Broth 2216 (marine broth 2216), containing 1.5% agar develops as 2 mm diameter colonies with smooth surface, orange yellow pigmentation, regular margin, and soft consistency. Diffusible pigments are not observed in this medium. Under phase contrast light microscopy, cocci are observed at 400× magnification. The cocci are well separated and isolated. They are Gram-positive and non-motile. The observed morphology classifies this organism as a member of *Micrococcaceae* family. Identification of the isolates was accomplished by comparing its 16S rRNA Polymerase Chain Reaction (PCR) with existing sequences available at the National Center for Biotechnology Information (NCBI) website (URL: http://www.ncbi.nlm.nih.gov/). Culture no. ZMA B-1 has been deposited with Microbial Type Culture Collection (MTCC), Institute of Microbial Technology, Sector 39-A, Chandigarh—160 036, India, a World Intellectual Property Organization (WIPO) recognized International Depository Authority (IDA) and has been given the accession number MTCC 5269.

In addition to the specific microorganism described herein, it should be understood that mutants, such as those produced by the use of chemical or physical mutagens including X-rays, U.V. rays etc. and organisms whose genetic makeup has been modified by molecular biology techniques, may also be cultivated to produce the compound PM 181104.

The screening for suitable mutants and variants which can produce the compound according to the invention can be confirmed by HPLC and/or determination of biological activity of the active compounds accumulated in the culture broth, for example by testing the compounds for antibacterial activity.

The medium and/or nutrient medium used for isolation and cultivation of culture no. ZMA B-1, which produces the compound PM181104, preferably contains sources of carbon, nitrogen and nutrient inorganic salts. The carbon sources are, for example, one or more of starch, glucose, sucrose, dextrin, fructose, molasses, glycerol, lactose, or galactose. A preferred carbon source is glucose. The sources of nitrogen are, for example, one or more of soybean meal, peanut meal, yeast extract, beef extract, peptone, malt extract, corn steep liquor, gelatin, or casamion acids. Preferred nitrogen sources are peptone and yeast extract. The nutrient inorganic salts are, for example, one or more of sodium chloride, potassium chloride, calcium chloride, magnesium chloride, strontium chloride, potassium bromide, sodium fluoride, sodium hydrogen phosphate, potassium hydrogen phosphate, disodium phosphate, calcium carbonate, sodium bicarbonate, sodium silicate, ammonium nitrate, potassium nitrate, sodium sulfate, ammonium sulphate, magnesium sulphate, ferric citrate or boric acid. Calcium carbonate, sodium chloride, and magnesium chloride are preferred.

The maintenance of culture no. ZMA B-1 may be carried out at a temperature ranging from 21° C. to 35° C. and a pH of about 6.5 to 8.5. Typically, culture no. ZMA B-1 is maintained at 27° C.-29° C. and a pH of about 7.4-7.8. The well-grown cultures may be preserved in the refrigerator at 4° C.-8° C.

Seed culture cultivation of culture no. ZMA B-1 may be carried out at a temperature ranging from 25° C. to 35° C. and a pH of about 6.5 to 8.5, for 20-55 hours at 200-280 rpm. Typically, culture no. ZMA B-1 seed is cultivated at 29° C.-31° C. and a pH of about 7.4-7.8, for 24-48 hours at 230-250 rpm.

The production of the compound PM181104 may be carried out by cultivating culture no. ZMA B-1 by fermentation at a temperature ranging from 26° C. to 36° C. and a pH of about 6.5 to 8.5, for 24-96 hours at 60-140 rpm and 100-200 lpm aeration. Typically, culture no. ZMA B-1 is cultivated at 30° C.-32° C. and pH 7.4-7.8 for 40-72 hours at 90-110 rpm and 140-160 lpm aeration.

The production of the compound PM181104 can be carried out by cultivating culture no. ZMA B-1 in a suitable nutrient broth under conditions described herein, preferably under submerged aerobic conditions, for example in shake flasks, as well as in laboratory fermenters. The progress of fermentation and production of the compound PM181104 can be detected by high performance liquid chromatography (HPLC) and by measuring the bioactivity of the culture broth against Staphylococci and/or *Enterococci* species by the known microbial agar plate diffusion assay method. The preferred culture is *Staphylococcus aureus* 3066, which is a strain resistant to methicillin, a β-lactam antibiotic reported in the literature, and *Enterococcus faecium* R2 (VRE) which is resistant to vancomycin. In the resulting culture broth, the compound PM181104 is present in the culture filtrate as well as in cell mass and can be isolated using known separation techniques such as solvent extraction and column chromatography. Thus, the compound PM181104 can be recovered from the culture filtrate by extraction at a pH of about 5 to 9 with a water immiscible solvent such as petroleum ether, dichloromethane, chloroform, ethyl acetate, diethyl ether or butanol, or by hydrophobic interaction chromatography using polymeric resins such as "Diaion HP-20®" (Mitsubishi Chemical Industries Limited, Japan), "Amberlite XAD®" (Rohm and Haas Industries U.S.A.), activated charcoal, or by ion exchange chromatography at pH 5-9. The active material can be recovered from the cell mass by extraction with a water miscible solvent such as methanol, acetone, acetonitrile, n-propanol, or iso-propanol or with a water immiscible solvent such as petroleum ether, dichloromethane, chloroform, ethyl acetate or butanol. One other option is to extract the whole broth with a solvent selected from petroleum ether, dichloromethane, chloroform, ethyl acetate, methanol, acetone, acetonitrile, n-propanol, iso-propanol, or butanol. Typically, the active material is extracted with ethyl acetate from the whole broth. Concentration and lyophilization of the extracts gives the active crude material.

The compound PM181104 of the present invention can be recovered from the crude material by fractionation using any of the following techniques: normal phase chromatography (using alumina or silica gel as stationary phase; eluents such as petroleum ether, ethyl acetate, dichloromethane, acetone, chloroform, methanol, or combinations thereof; and additions of amines such as $NEt_3$); reverse phase chromatography (using reverse phase silica gel such as dimethyloctadecylsilylsilica gel, (RP-18) or dimethyloctylsilyl silica gel (RP-8) as stationary phase; and eluents such as water, buffers (for example, phosphate, acetate, citrate (pH 2-8)), and organic solvents (for example, methanol, acetonitrile, acetone, tetrahydrofuran, or combinations of these solvents)); gel permeation chromatography (using resins such as Sephadex LH-20® (Pharmacia Chemical Industries, Sweden), TSK-gel® Toyopearl HW (TosoHaas, Tosoh Corporation, Japan) in solvents such as methanol, chloroform, acetone, ethyl acetate, or their combinations, or Sephadex® G-10 and G-25 in water); or by counter-current chromatography (using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is chromatography over reverse phase silica gel (RP-18).

The compound PM181104 and isomers thereof, can be converted into their pharmaceutically acceptable salts, which are all contemplated by the present invention. The salts can be prepared by standard procedures known to one skilled in the art, for example, salts like sodium and potassium salts, can be prepared by treating the compound PM181104 and isomers thereof, with a suitable sodium or potassium base, for example sodium hydroxide, potassium hydroxide.

The esters and ethers of the compound PM181104 represented by formula I, can be prepared by the methods given in the literature (Advanced Organic Chemistry, 1992, $4^{th}$ Edition, J. March, John Wiley & Sons). Esters can also be prepared by the method described in the literature (J. Med. Chemistry, 1992, 35, 145-151). In a preferred embodiment of the invention, the compounds of formula I wherein R is alkyl, cycloalkyl, aryl or heterocyclyl are prepared by reacting PM181104 with an appropriate acid having the formula RCOOH; wherein R is alkyl, cycloalkyl, aryl or heterocyclyl, in the presence of a coupling agent such as dicyclohexyl carbodimide (DCC) and catalytic amounts of a base such as dimethylamino pyridine (DMAP).

The phosphate esters can be prepared by a method reported in the literature (Bioorganic & Medicinal Chemistry Letters, 1994, vol 4, No. 21, 2567-2572). Ethers can be prepared by the method as described in the U.S. Pat. No. 7,022,667, which is incorporated herein by reference.

The compound PM181104 has antibacterial activity against a wide range of bacterial strains. The compound PM181104, stereoisomers, pharmaceutically acceptable salts and derivatives such as esters and ethers thereof, alone or together, can be administered to animals, such as mammals, including humans, as pharmaceuticals and in the form of pharmaceutical compositions. Accordingly, the present invention also relates to the compound PM181104, its stereoisomers, its pharmaceutically acceptable salts and its ester and ether derivatives for use as pharmaceuticals and to the use of the compound PM181104, stereoisomers, pharmaceutically acceptable salts and its ester and ether derivatives for the production of medicaments having antibacterial activity.

The present invention further relates to pharmaceutical compositions which contain an effective amount of the compound PM181104 and/or stereoisomers and/or one or more pharmaceutically acceptable salts and/or derivatives particularly the esters and ethers thereof, together with a pharmaceutically acceptable carrier. The effective amount of the compound PM181104, or its stereoisomers, or its pharmaceutically acceptable salts or its derivatives as the active ingredient in the pharmaceutical preparations normally is from about 0.01 mg to 100 mg.

The present invention also relates to a method for the preparation of a medicament containing the compound PM181104 and/or stereoisomers and/or one or more pharmaceutically acceptable salts and/or ester and ether derivatives thereof, for the treatment and prevention of diseases caused by bacterial infections.

The compounds of the present invention are particularly useful as anti-bacterial agents. The present invention accordingly relates to the use of the compound PM181104 and/or stereoisomers and/or one or more pharmaceutically acceptable salts and/or derivatives thereof, for the manufacture of a medicament for the prevention or treatment of diseases caused by bacterial infections. The bacterial infections for the treatment of which the compounds of the present invention are used may be caused by bacteria belonging to *Staphylococcus, Streptococcus, Enterococcus* and *Bacillus* species.

The term "*Staphylococcus* species" refers to a Gram-positive bacteria, which appears as grape-like clusters when viewed through a microscope and as large, round, golden-yellow colonies, often with β-hemolysis, when grown on blood agar plates. *Staphylococcus aureus* which belongs to *Staphylococcus* species causes a variety of suppurative (pus-forming) infections such as superficial skin lesions such as boils, styes and furunculosis; more serious infections such as pneumonia, mastitis, phlebitis, meningitis, and urinary tract infections; and deep-seated infections, such as osteomyelitis and endocarditis. *Staphylococcus aureus* is a major cause of hospital acquired (nosocomial) infection of surgical wounds and infections associated with indwelling medical devices. *Staphylococcus aureus* causes food poisoning by releasing enterotoxins into food, and toxic shock syndrome by release of superantigens into the blood stream.

The term "*Streptococcus* species" refers to a genus of spherical, Gram-positive bacteria, and a member of the phylum Firmicutes. Streptococci are lactic acid bacteria. *Streptococcus* species are responsible for infectious diseases such as meningitis, bacterial pneumonia, endocarditis, erysipelas and necrotizing fasciitis (the 'flesh-eating' bacterial infections).

The term "*Enterococcus* species" refers to a genus of lactic acid bacteria of the phylum Firmicutes. They are Gram-positive cocci which often occur in pairs (diplococci). Enterococci are facultative anaerobic organisms. Enterococci are among the most frequent causes of hospital-acquired infections. Enterococci develop resistance to antibiotics such as gentamicin and vancomycin.

The term "*Bacillus* species" refers to a large number of diverse, rod-shaped Gram positive bacteria that are motile by peritrichous flagella and are aerobic. It is also a member of the division Firmicutes. Members of this genus are capable of producing endospores that are highly resistant to unfavorable environment conditions. *Bacillus cereus* which belongs to *Bacillus* species causes two types of food-borne intoxications. One type is characterized by the symptoms of nausea, vomiting and abdominal cramps. The second type is manifested primarily by abdominal cramps and diarrhea. Infections attributed to *Bacillus subtilis* which belongs to *Bacillus* species, include bacteremia, endocarditis, pneumonia, and septicemia in patients in compromised immune states.

The compounds of the present invention can be administered orally, nasally, topically, subcutaneously, intramuscularly, intravenously, or by other modes of administration.

Pharmaceutical compositions which contain PM181104 or a stereoisomer or a pharmaceutically acceptable salt or an ester or ether derivative thereof, with other pharmaceutically active substances can be prepared by mixing the active compounds with one or more pharmacologically tolerated auxiliaries and/or excipients such as, wetting agents, solubilisers such as surfactants, vehicles, tonicity agents, fillers, colorants, masking flavors, lubricants, disintegrants, diluents, binders, plasticizers, emulsifiers, ointment bases, emollients, thickening agents, polymers, lipids, oils, cosolvents, complexation agents, or buffer substances, and converting the mixture into a suitable pharmaceutical form such as, for example, tablets, coated tablets, capsules, granules, powders, creams, ointments, gels, syrup, emulsions, suspensions, or solutions suitable for parenteral administration.

Examples of auxiliaries and/or excipients that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegtetable oil, organic and mineral waxes, paraffin, gels, propylene glycol, benzyl alcohol, dimethylacetamide, ethanol, polyglycols, tween 80, solutol HS 15, and water.

It is also possible to administer the active substances as such, without vehicles or diluents, in a suitable form, for example, in capsules.

As is customary, the galenic formulation and the method of administration as well as the dosage range which are suitable in a specific case depend on the species to be treated and on the state of the respective condition or disease, and can be optimized using methods known in the art. On average, the daily dose of active compound in a patient is 0.0005 mg to 15 mg per kg, typically 0.001 mg to 7.5 mg per kg.

The following are provided as illustrative examples of the present invention and do not limit the scope thereof:

Example 1

Isolation of Culture No. ZMA B-1 from Marine Source a) Composition of the Isolation Medium:
Zobell Marine Broth 2216 (Agarified by 1.5% Agar Agar)

Peptic digest of animal tissue 5.0 g, yeast extract 1.0 g, ferric citrate 0.1 g, sodium chloride 19.45 g, magnesium chloride 8.8 g, sodium sulphate 3.24 g, calcium chloride 1.8 g, potassium chloride 0.55 g, sodium bicarbonate 0.16 g, potassium bromide 80.0 mg, strontium chloride 34.0 mg, boric acid 22.0 mg, sodium silicate 4.0 mg, sodium fluorate 2.4 mg, ammonium nitrate 1.6 mg, disodium phosphate 8.0 mg, agar powder 15.0 g, double distilled water 1.0 L, final pH (at 25° C.) 7.4-7.8.

b) Procedure

The sponge sample, *Spirastrella inconstans* var. *digitata* (Dendy) was collected from Palk Bay, Tamil Nadu coast, India, by SCUBA diving, from a depth of three meters. The sponge sample was rinsed in sterile seawater and immediately transferred into sterile polyethene containers. The containers were stored at −20° C. and transported by maintaining the temperature below 0° C., to the laboratory for further studies. On reaching the lab, the sponge samples were stored at less than 0° C. and later thawed to room temperature (25±2° C.)

just before isolation of the culture. The sponge sample was cut aseptically into 2×2 cm pieces and suspended in 5 mL of sterile seawater in a 25 mL sterilized test tube. The test tube was vortexed for 30 seconds; the seawater was drained out and fresh seawater was added. The same process was repeated three times. Finally, the seawater was drained out and the sponge piece was placed on petri plates containing above mentioned isolation medium [Zobell Marine Broth 2216 (agarified by 1.5% agar agar); HiMedia]. The petri plate was incubated at room temperature (25±2° C.) till growth was observed in the plates. The colonies grown on the plates were isolated on the basis of colony characteristics and streaked on petri plates containing above mentioned isolation medium [Zobell Marine Broth 2216 (agarified by 1.5% agar agar); HiMedia]. The isolates were repeatedly subcultured till pure culture no. ZMA B-1 was obtained. The culture no. ZMA B-1 was thus isolated from amongst the growing microorganisms as a single isolate.

Example 2

Purification of Culture No. ZMA B-1 a) Composition of the Isolation Medium:
Zobell Marine Broth 2216 (Agarified by 1.5% Agar Agar)
Peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluorate 2.4 mg, ammonium nitrate 1.6 mg, disodium phosphate 8.0 mg, agar 15.0 g, demineralised water 1.0 L, pH 7.4-7.8.
b) Procedure:
The culture was available on Zobell Marine Broth 2216 (agarified by 1.5% agar agar) in 15 mm diameter petriplate. The growth on the petriplate was streaked on Zobell Marine Broth 2216 (agarified by 1.5% agar agar) slant. The slant was incubated for 2 days at 25° C. One of the single colonies from the upper portion of the slant bed was transferred to fresh slants. The slants were incubated for 2 days at 25° C. These were then used for shake flask fermentation for the purpose of primary anti-infective screening.

Example 3

Maintenance of Producer Strain

Culture No. ZMA B-1 a) Composition of the Medium (Zobell Marine Broth 2216):
Peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluorate 2.4 mg, ammonium nitrate 1.6 mg, disodium phosphate 8.0 mg, agar 15.0 g, demineralised water 1.0 L, pH 7.4-7.8.
b) After dissolving the ingredients thoroughly by heating, the resultant solution was distributed in test tubes and sterilized at 121° C. for 30 min. The test tubes were cooled and allowed to solidify in a slanting position. The agar slants were streaked with the growth of culture no. ZMA B-1 by a wire loop and incubated at 27-29° C. until a good growth was observed. The well-grown cultures were stored in the refrigerator at 4-8° C.

Example 4

Fermentation of the Culture No. ZMA B-1 in Shake Flasks a) Composition of Seed Medium (Zobell Marine Broth 2216):
Peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluorate 2.4 mg, ammonium nitrate 1.6 mg, disodium phosphate 8.0 mg, demineralised water 1.0 L, pH 7.4-7.8.
b) The above medium was distributed in 40 ml amounts in 500 ml Erlenmeyer flasks and autoclaved at 121° C. for 30 mins. The flasks were cooled to room temperature and each flask was inoculated with a loopful of the well-grown producing strain (culture no. ZMA B-1) on the slant and shaken on a rotary shaker for 24-48 hours at 230-250 rpm at 30° C. (±1° C.) to give seed culture.
c) Composition of the Production Medium:
Peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluorate 2.4 mg, ammonium nitrate 1.6 mg, disodium phosphate 8.0 mg, demineralised water 1.0 L, pH 7.4-7.8
d) 40 ml of the production medium in 500 ml capacity Erlenmeyer flasks was autoclaved at 121° C. for 30 mins, cooled to 29-30° C. and seeded with 2 ml of the seed culture mentioned in example 4b.
e) Fermentation Parameters
Temperature 29-30° C.; agitation 230-250 rpm; harvest time 48-72 hours.
The production of the compound PM181104 in the fermentation broth was determined by testing the bioactivity against *Enterococcus faecium* R2 (VRE) and/or *S. aureus* 3066 MRSA strain using the agar well diffusion method. The harvest pH of the culture broth was 7.0-8.0. The culture broth was harvested and the whole broth was used for bioactivity testing, which is indicative of presence of the compound PM181104 in the fermented broth.

Example 5

Preparation of Seed Culture in Shake Flasks for Fermentation a) Composition of the Medium:
Peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluorate 2.4 mg, ammonium nitrate 1.6 mg, disodium phosphate 8.0 mg, demineralised water 1.0 L, pH 7.4-7.8.

b) The above medium was distributed in 200 ml amounts in 1 L Erlenmeyer flasks and autoclaved at 121° C. for 30 mins. The flasks were cooled to room temperature and each flask was inoculated with a loopful of the well-grown producing strain (culture no. ZMA B-1) on the slant and shaken on a rotary shaker for 24-48 hours at 230-250 rpm at 29-31° C. to give a seed culture.

Example 6

Cultivation of the Culture No. ZMA B-1 in Fermenter a) Composition of the Production Medium:

Glucose 50.0 g, yeast extract 11.0 g, peptone 4.0 g, beef extract 4.0 g calcium carbonate 5 g, sodium chloride 2.5 g, demineralized water 1 L, pH 7.6 (before sterilization).

b) 250 L of the production medium in 300 L fermenter along with 80 ml of desmophen as an antifoaming agent was sterilized in situ for 30 mins. at 121° C., cooled to 29-31° C. and seeded with 6 L of the seed culture mentioned in example 5b.

c) Fermentation Parameters:

Temperature 30-32° C.; agitation 100 rpm; aeration 150 lpm; harvest time 44-66 hours.

The production of the compound PM181104 in the fermentation broth was determined by testing the bioactivity against *S. aureus* 3066 (MRSA strain) and/or *Enterococcus faecium* R2 (VRE) using the agar well diffusion method. The harvest pH of the culture broth was 7.0-8.0. The culture broth was harvested and the whole broth was used for isolation and purification of the compound PM181104.

Example 7

Isolation and Purification of the Compound PM181104

The whole broth (240 L) of Example 6 was harvested and extracted using ethyl acetate (240 L) by stirring in a glass vessel. The organic layer was separated using disc stack separator (Alfa-laval, model No. LAPX404) and concentrated to obtain the crude extract (296 g). The crude material obtained was stirred and sonicated for 30 min using petroleum ether (3×1 L) and filtered to obtain insoluble residue (38 g), which was chromatographed by vacuum liquid chromatography using following method.

The insoluble residue (35.5 g) was dissolved in a mixture of methanol and acetonitrile (3:1, 400 ml) and preadsorbed on to LiChroprep RP-18 [25-40μ, 40 g] and applied to a fritted filter funnel (G-4 grade; 10 cm×10.5 cm) packed with LiChroprep RP-18 (25-40μ, 110 g) adsorbent. Elution using house vacuum (100-120 mm) was done initially with water (4 L), followed by water:methanol (1:1, 5 L), methanol (3 L), methanol:acetonitrile (2.5 L) and acetonitrile. The monitoring of the purification was done by bioassay against *Ent. faecium* R2 and/or *S. aureus* 3066 and/or analytical HPLC. The compound PM181104 was detected in methanol and methanol:acetonitrile & acetonitrile fractions. Like fractions were pooled and concentrated to obtain the semi pure material (1.826 g).

The final purification was done by repeated preparative HPLC using the following conditions:

| Column | Eurospher RP-18 (10μ, 32 × 250 mm) |
|---|---|
| Eluent | acetonitrile:water (56:44) |
| Flow rate | 50 ml/min |
| Detection (UV) | 220 nm |
| Retention time | 12-14 min |

Purity of fractions was checked by bioassay against *Ent. faecium* R2 and/or *S. aureus* 3066 and/or analytical HPLC. The eluates containing the compound PM181104 were pooled and concentrated under reduced pressure to remove the solvent to obtain 600 mg of pure compound.

The physico-chemical and spectral properties of the compound PM181104

| | |
|---|---|
| Appearance | White amorphous solid |
| Melting point | >300° C. (decomposes) |
| Solubility | Methanol, DMSO |
| HPLC | Rt 5.61 mins |
| Column | Kromasil C18 (5μ; 150 × 4.6 mm I.D.) (column temperature 40° C.) |
| Mobile phase | acetonitrile:water (1:1) |
| Injection vol. | 10 μl (0.1 mg/ml concentration in mobile phase) |
| Flow rate | 1 ml/min |
| Detection | 220 nm |
| HR-ESI(+)MS m/z | 1515.3733 (M + H) |
| Mol. Formula | $C_{69}H_{66}N_{18}O_{13}S_5$ |
| Mol. Weight | 1514 |
| UV (MeOH) | 205.2, 220.6 and 306.2 nm (refer to FIG. 1) |
| IR (KBr) | 3368, 2981, 1654, 1516, 1429, 1314, 1199, 1269, 1074, 1034, 805, 580 cm$^{-1}$ (refer to FIG. 2) |
| $^1$H NMR | refer to table 1 and FIG. 3 |
| $^{13}$C NMR | refer to table 2 and FIG. 4 |

TABLE 1

$^1$H NMR of the compound PM181104 in DMSO-$d_6$

| Peak | δ |
|---|---|
| 1 | 1.33-1.34 (d, 3H) |
| 2 | 1.94 (m, 4H) |
| 3 | 2.05-2.06 (br m, 1H) |
| 4 | 2.12 (br m, 1H) |
| 5 | 2.25-2.28 (br d, 1H) |
| 6 | 2.40-2.42 (br m, 1H) |
| 7 | 2.68 (s, 3H) |
| 8 | 2.76-2.82 (m, 2H) |
| 9 | 2.97-2.99 (d, 1H) |
| 10 | 3.17-3.21 (m, 1H) |
| 11 | 3.24-3.26 (m, 1H) |
| 12 | 3.62 (t, 2H) |
| 13 | 3.69 (m, 1H) |
| 14 | 3.77 (s, 2H) |
| 15 | 4.49-4.50 (d, 1H) |
| 16 | 4.69-4.71 (t, 1H) |
| 17 | 4.80 (m, 1H) |
| 18 | 4.89 (m, 1H) |
| 19 | 4.93-4.97 (t, 1H) |
| 20 | 5.23 (t, 1H) |
| 21 | 5.33 (m, 1H) |
| 22 | 5.52 (s, 1H) |

TABLE 1-continued

¹H NMR of the compound PM181104 in DMSO-d₆

| Peak | δ |
|---|---|
| 23 | 5.63 (s, 1H) |
| 24 | 5.83 (s, 1H) |
| 25 | 5.92 (s, 1H) |
| 26 | 6.07 (s, 1H) |
| 27 | 6.50 (s, 1H) |
| 28 | 6.59-6.61 (d, 2H) |
| 29 | 6.86 (s, 1H) |
| 30 | 7.04-7.06 (d, 2H) |
| 31 | 7.17-7.18 (m, 1H) |
| 32 | 7.26 (d, 4H) |
| 33 | 7.30 (s, 1H) |
| 34 | 7.33-7.35 (d, 1H) |
| 35 | 7.53 (s, 1H) |
| 36 | 7.69 (s, 1H) |
| 37 | 7.90 (s, 1H) |
| 38 | 7.95 (s, 1H) |
| 39 | 8.27-8.29 (d, 2H) |
| 40 | 8.49-8.50 (d, 1H) |
| 41 | 8.57-8.58 (d, 1H) |
| 42 | 8.65 (s, 1H) |
| 43 | 8.81 (t, 2H) |
| 44 | 9.07 (s, 1H) |
| 45 | 9.16 (s, 1H) |
| 46 | 9.48 (s, 1H) |
| 47 | 10.03 (s, 1H) |

TABLE 2

¹³C NMR of the compound PM181104 in DMSO-d₆

| signal | δ |
|---|---|
| 1 | 12.04 |
| 2 | 16.88 |
| 3 | 25.16* |
| 4 | 29.42 |
| 5 | 33.09 |
| 6 | 36.67 |
| 7 | 37.00 |
| 8 | 38.62 |
| 9 | 38.73 |
| 10 | 47.22 |
| 11 | 47.76 |
| 12 | 47.88 |
| 13 | 48.88 |
| 14 | 52.69 |
| 15 | 54.43 |
| 16 | 59.92 |
| 17 | 60.56 |
| 18 | 77.80 |
| 19 | 103.89 |
| 20 | 104.94 |
| 21 | 107.52 |
| 22 | 115.46* |
| 23 | 116.92 |
| 24 | 118.77 |
| 25 | 122.84 |
| 26 | 123.39 |
| 27 | 124.33 |
| 28 | 127.08 |
| 29 | 127.36 |
| 30 | 128.71* |
| 31 | 129.18 |
| 32 | 129.76* |
| 33 | 130.11 |
| 34 | 130.99* |
| 35 | 133.99 |
| 36 | 135.17 |
| 37 | 136.87 |
| 38 | 137.67 |
| 39 | 140.92 |
| 40 | 147.97 |
| 41 | 149.73 |
| 42 | 150.83 |
| 43 | 151.04 |
| 44 | 152.08 |
| 45 | 153.43 |
| 46 | 154.20 |
| 47 | 156.27 |
| 48 | 156.45 |
| 49 | 159.06 |
| 50 | 161.27 |
| 51 | 161.54* |
| 52 | 162.79 |
| 53 | 163.35 |
| 54 | 165.58 |
| 55 | 167.95 |
| 56 | 169.68 |
| 57 | 170.39 |
| 58 | 171.03 |
| 59 | 171.77 |
| 60 | 171.96 |
| 61 | 173.51 |
| 62 | 174.14 |
| 63 | 174.90 |

*two carbons

Biological Evaluation of the Compound PM181104

In-Vitro Assay

Example 8

The in-vitro potency was established by minimum inhibitory concentration (MIC) determinations of the compound PM181104 against bacterial strains, by using the Macro-broth dilution method as per National Committee for Clinical Laboratory Standards (2000) guidelines [Journal of Antimicrobial Chemotherapy, 2002, 50, 125-128 (Cross Reference 8: Methods for Dilution Antimicrobial Susceptibility Tests for Bacteria that Grow Aerobically-Fifth Edition: Approved Standard M7-A5. NCCLS, Wayne, Pa., USA)]. Unless stated otherwise, Mueller-Hinton broth was used as nutrient medium for the assay. Linezolid (manufactured by Glenmark Pharma Ltd; Batch no: K2005028) was used as known standard in all in-vitro experiments. For preparation of the stock solution the compound PM181104 was dissolved in chloroform (5% of the total required volume) and diluted using methanol (95% of the total required volume).

Result:

The results obtained are shown in Table 3 below, and demonstrate that the compound PM181104 has utility in treating bacterial infections.

TABLE 3

MICs of the compound PM181104 against bacterial strains

| Test organism | MIC (μg/ml) |
|---|---|
| S. aureus KEM-MRSA1 | 0.03125 |
| S. aureus KEM-MRSA2 | 0.03125 |
| S. aureus KEM-MRSA7 | 0.01563 |
| S. aureus KEM-MRSA8 | 0.01563 |
| S. aureus KEM-MRSA11 | 0.0625 |
| S. aureus KEM-MRSA12 | 0.01563 |
| S. aureus KEM-MRSA18 | 0.01563 |

TABLE 3-continued

MICs of the compound PM181104 against bacterial strains

| Test organism | MIC (µg/ml) |
|---|---|
| S. aureus KEM-MRSA19 | 0.00781 |
| S. aureus KEM-MRSA20 | 0.01563 |
| S. aureus KEM-MRSA21 | 0.01563 |
| S. aureus KEM-MRSA22 | 0.00781 |
| S. aureus KEM-MRSA23 | 0.01563 |
| S. aureus KEM-MRSA24 | 0.00781 |
| S. aureus KEM-MRSA25 | 0.01563 |
| S. aureus Lilavati-MRSA3 | 0.01563 |
| S. aureus Rehaja-MRSA1 | 0.03125 |
| S. aureus Bom-MRSA2 | 0.0625 |
| Staphylococcus aureus subsp. aureus ATCC 33591 | 0.03125 |
| S. aureus (789) | 0.00781 |
| S. aureus (20666) | 0.01563 |
| S. aureus (3066) | 0.03125 |
| S. aureus SG511 | 0.0625 |
| S. aureus wien8 | 0.01563 |
| S. aureus wien13 | 0.0625 |
| S. aureus C1 3184 | 0.0625 |
| S. aureus (E710) | 0.03125 |
| S. aureus ATCC29213 | 0.03125 |
| S. epidermidis 5744IW | 0.01563 |
| S. epidermidis Pat 01 IV | 0.0625 |
| S. epidermidis 823 | 0.03125 |
| S. epidermidis 6098 | 0.0625 |
| S. epidermidis 6493II(2)W | 0.0625 |
| S. epidermidis 10221II W | 0.00781 |
| S. epidermidis 32965 | 0.03125 |
| S. haemolytica 809 | 0.0625 |
| Enterococci KEM-VRE26 | 0.00781 |
| Enterococci KEM-VRE27 | 0.00391 |
| Enterococci KEM-VRE28 | 0.00781 |
| Enterococci KEM-VRE29 | 0.00391 |
| E. faecium (R-2) | 0.00781 |
| E. faecium (VR-1) | 0.00781 |
| E. faecium D-59 | 0.00781 |
| E. faecium D 18F | 0.00781 |
| E. faecium (O2-D3IP1) | 0.00391 |
| E. faecium 4045H | 0.00781 |
| E. faecalis (FH-1) | 0.00391 |
| E. faecalis (uD.8b) | 0.00391 |
| E. faecalis 4073H | 0.00781 |
| E. faecium ATCC 51559 | 0.00781 |
| E. faecalis, ATCC 51299 | 0.01563 |
| E. faecalis ATCC 51575 | 0.03125 |
| E. faecalis ATCC BAA 472 | 0.01563 |
| B. cereus | 0.00391 |
| B. subtilis ATCC 6633 | 0.00781 |
| B. subtilis | 0.01563 |
| B. megaterium FH 1127 | 0.00781 |
| B. firmus | 0.01563 |
| Streptococcus hirae 55 | 0.00391 |
| Streptococcus equinus 02 D5 Gr1 | 0.01563 |
| Streptococcus durans 4939 (1) H | 0.00781 |
| Streptococcus durans | 0.00781 |
| Salmonella typhi Para A | >1 |
| Pse. aeruginosa (M-35) | >1 |
| Klebsiella pneumoniae | >1 |
| Citrobacter diversus 2046 E | >1 |
| E. coli SS | >1 |

Abbreviations used in table 3 are -
S: *Staphylococcus*
E: *Enterococci*
B: *Bacillus*

In-Vivo Assay

The in-vivo potency was established by protection dose (PD) determinations of the compound PM181104 for its antibiotic activity in three animal models using either male or female Balb/C mice.

The models used were the general purpose efficacy testing models and organ/tissue specific efficacy testing models. The general purpose efficacy testing models used were systemic infection model (septicemia), and localized infection model (neutropenic thigh model). The Organ/Tissue specific infection models used for efficacy testing were kidney, lung infection, and skin abscess model.

Example 9

Systemic Infection Model

The animals were infected intraperitoneally with ~$10^8$ to $10^9$ cfu of an overnight grown culture of methicillin resistant *Staphylococcus aureus* E710 (MRSA), suspended in normal saline (0.85% sodium chloride). PM181104 solution was prepared in cremophor-ethanol formulation as described in example 14. The solution was administered intravenously at 5 mg, 2.5 mg and 1.25 mg/kg doses, immediately after infection. Each experimental group consisted of ten animals. The $PD_{100}$ of PM181104 for the septicemia model was determined to be 5 mg/kg as compard to standard antibiotic Linezolid (manufactured by Glenmark Pharma Ltd; Batch no: K2005028) that showed $PD_{100}$ at 25 mg/kg.

Example 10

Neutropenic Thigh Model

Mice were made neutropenic with cyclophosphamide (150 mg and 100 mg/kg) at 96 hrs and 24 hrs, respectively, prior to infection with *S. aureus* E-710. The animals were infected in the thighs intramuscularly with ~$10^7$ cfu of an overnight grown culture of *S. aureus* E-710, suspended in normal saline (0.85% sodium chloride). Each experimental group consisted of six animals. PM181104 was prepared in cremophor-ethanol formulation as described in example 14. The solution was administered intravenously at 5 mg/kg dose, two hours post infection. The animals were sacrificed at various time points and the thigh tissue harvested to determine the viable counts. A decrease of approximately 1 log was observed with PM181104 at 5 mg/kg dose, at 6 hour time point, which was comparable with the standard antibiotic used viz. Linezolid (manufactured by Glenmark Pharma Ltd; Batch no: K2005028) at 25 mg/kg dose.

Example 11

Kidney Infection Model 0.2 ml of 2% λ Carrageenan was administered intravenously to Balb/C mice 7 days prior to infection. Overnight grown log phase culture of *Enterococcus faecium* ATCC 47077 adjusted to approximately $10^9$ cfu/ml, was injected intravenously to the mice at a volume of 0.2 ml. PM181104 solution, prepared in cremophor-ethanol formulation as described in example 14, was administered intravenously to the mice at 4 hours, 24 hours and 48 hours post-infection. At 72 hours post infection, the animals were sacrificed and kidneys were harvested to determine the bacterial load. A decrease in bacterial count of approximately 1 log was observed with PM181104 at 5 mg/kg dose, which was comparable with the standard antibiotics used viz. Linezolid (manufactured by Glenmark Pharma Ltd; Batch no: K2005028) at 25 mg/kg and Vancomycin hydrochloride (manufactured by HiMedia; Catalogue no: RM217-500 mg; Lot no: 06-0350) at 150 mg/kg dose.

Example 12

Lung Infection Model

Balb/C mice were rendered neutropenic by intraperitoneally administering 200 mg/kg cyclophosphamide four days and two days prior to infection. On the day of infection, the mice were anesthetized and infected with *S. aureus* E-710 log-phase culture suspension having bacterial density of approximately $10^6$ to $10^7$ cfu/ml. 24 and 36 hours post infection the first and second respective dose of drug was administered intravenously. 48 hours post infection, the animals were humanely euthanized and their lungs were aseptically collected to determine the viable count of bacteria. In this model, PM181104 was tested at 5 mg/kg dose prepared in cremophor-ethanol formulation as described in example 14. Two standard antibiotics viz. Linezolid (80 mg/kg single dose at 24 hours post infection) and Vancomycin (110 mg/kg, two doses at 24 and 48 hours post infection) were used as positive controls. PM181104 showed bacteriostatic activity, which was comparable to Linezolid (manufactured by Glenmark Pharma Ltd; Batch no: K2005028) standard. Vancomycin hydrochloride (manufactured by HiMedia; Catalogue no: RM217-500 mg; Lot no: 06-0350) standard showed a bactericidal profile. There was approximately 2 log difference in the bacterial count in the lungs of animals treated with PM181104 as compared to that in untreated control animals.

Example 13

Skin Abscess Model

Balb/C mice were infected subcutaneously with approximately 108 cfu of an overnight grown culture of methicillin resistant *S. aureus* E710 (MRSA). The bacteria were suspended in 1:1 mixture of 2% cytodex beads in normal saline (0.85% sodium chloride). PM181104 was prepared in cremophor-ethanol formulation as described in example 14. The solution was administered intravenously at 2.5 mg, 5 mg and 10 mg/kg doses, two hours post infection. Each experimental group consisted of six animals. Following abscess formation the animals were sacrificed and abscess harvested to determine the viable counts. A decrease in bacterial count of approximately 1 log was observed with PM181104 at 5 mg/kg dose, which was comparable with the standard antibiotic used viz. Linezolid (manufactured by Glenmark Pharma Ltd; Batch no: K2005028) at 50 mg/kg dose.

Formulation of the Compound PM181104

Example 14

Injectable Formulations Were Prepared by the Following General Method

Ethanol and cremophor EL were mixed in 1:1 proportion (by weight). To this, PM181104 was added and vortexed. This mixture was sonicated at 25° C. This mixture (considering it as 10% constituent) was diluted by adding water (90%), and vortexed to obtain the injectable formulation.

Derivatives of the Compound PM181104

Example 15

Butyric Acid Ester Derivative of PM181104

To a solution of PM181104 (0.13 g, 0.085 mmol) in dichloromethane (2 ml), butyric acid (0.008 µl, 0.085 mmol), DCC (0.018 g, 0.085 mmol) and catalytic amount of DMAP (0.002 g, 0.016 mmol) were added and the reaction mixture was stirred for 18 h under nitrogen atmosphere. To the reaction mixture, cold water was added and the organic layer was separated; the aqueous layer was extracted with dichloromethane (3×50 ml), organic extracts were pooled and washed with water (2×30 ml). The organic layer was dried over anhydrous sodium sulphate and concentrated. The crude product was purified using column chromatography [silica gel (60-120 mesh], 4% methanol in chloroform] to obtain the title compound as white solid. Yield: 0.11 g (81%); MS m/z (ESI): 1585 (M+H)

Butyric acid ester derivative of PM181104 showed MIC value of 2.5 µg/ml against *E. faecium* R-2, (VRE) bacterial strain.

Example 16

Stearic Acid Ester Derivative of PM181104

To a solution of PM181104 (0.12 g, 0.079 mmol) in dichloromethane (2 ml), stearic acid (0.022 µl, 0.079 mmol), DCC (0.016 g, 0.079 mmol) and catalytic amount of DMAP (0.002 g, 0.016 mmol) were added and the reaction mixture was stirred for 6 h under nitrogen atmosphere. To the reaction mixture, cold water was added and the organic layer was separated; the aqueous layer was extracted with dichloromethane (3×50 ml), organic extracts were pooled and washed with water (2×30 ml). The organic layer was dried over anhydrous sodium sulphate and concentrated. The crude product was purified using column chromatography [silica gel (60-120 mesh], 4% methanol in chloroform] to obtain the title compound as white solid. Yield: 0.1 g (71%); MS m/z (ESI): 1781 (M+H).

Stearic acid ester derivative of PM181104 showed MIC value of 1.25 µg/ml against *E. faecium* R-2, (VRE) bacterial strain.

Example 17

Nicotinic Acid Ester Derivative of PM181104

To a solution of PM181104 (0.02 g, 0.013 mmol) in N,N-dimethylformamide (1 ml), nicotinic acid (0.008 g, 0.065 mmol), DCC (0.014 g, 0.065 mmol) and catalytic amount of DMAP (0.0008 g, 0.0065 mmol) were added and the reaction mixture was stirred for 18 h under nitrogen atmosphere. Solvent was removed and to the residue 10 ml of dichloromethane was added. The undissolved urea was filtered and the filtrate was washed with water (2×10 ml). The organic layer was dried over anhydrous sodium sulphate and concentrated to dryness. The crude product was purified by column chromatography [C-18 reverse phase column (Eurosphere, 20 nm), 55% acetonitrile in water] to obtain the title compound as white solid. Yield: 0.011 g (56%); MS m/z (ESI): 1621 (M+H).

The nicotinic acid ester derivative of PM181104 was tested against bacterial strains. The results obtained are shown in table 4 below, and demonstrate that the nicotinic acid ester derivative of PM181104 has utility in treating bacterial infections.

TABLE 4

MICs of nicotinic acid ester derivative of PM181104 against bacterial strains

| Test organism | MIC (µg/ml) |
| --- | --- |
| E. faecalis ATCC 51299 | 0.312 |
| E. faecalis ATCC 51575 | 0.312 |
| E. faecalis ATCC BAA472 | 0.312 |
| E. faecium ATCC 51559 | 0.156 |
| E. faecium R-2 (VRE) | 0.312 |
| S. aureus MRSA ATCC 33591 | >10 |
| S. aureus MRSA E710 | >10 |

We claim:

1. A compound of formula I:

Formula I wherein R is H, alkyl, alkylcarbonyl, $(HO)_2PO-$, alkyl-OPO(OH)—, $(alkyl-O)_2PO-$, cycloalkyl, cycloalkylcarbonyl, aryl, arylcarbonyl, heterocyclyl or heterocyclyl carbonyl; or a pharmaceutically acceptable salt thereof, wherein if R is H then the compound is isolated.

2. The compound as claimed in claim 1, wherein R is H, named PM 181104, or a pharmaceutically acceptable salt thereof.

Figure 1:
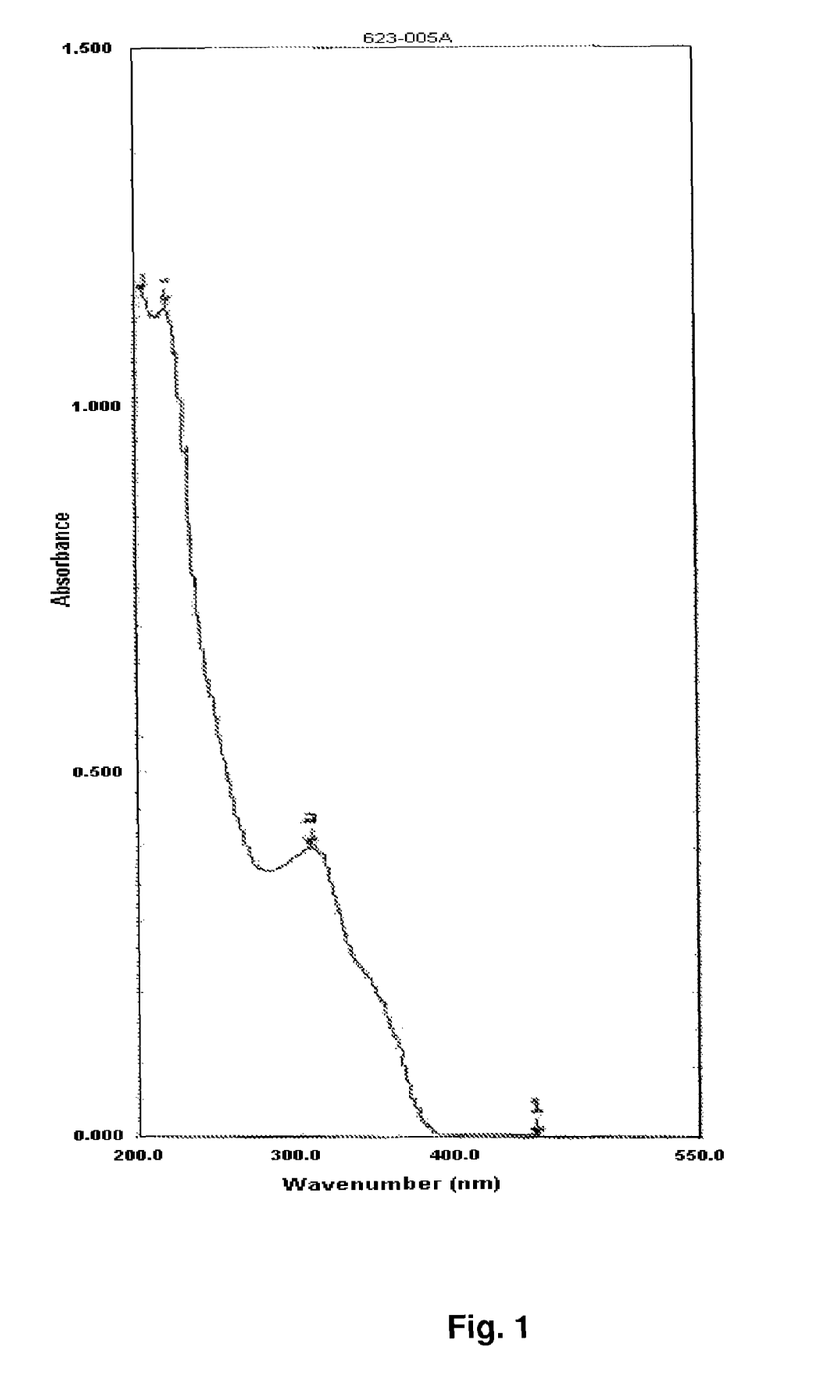
FIG. 1 shows the ultraviolet absorption (UV) spectrum of PM181104.
Figure 2:
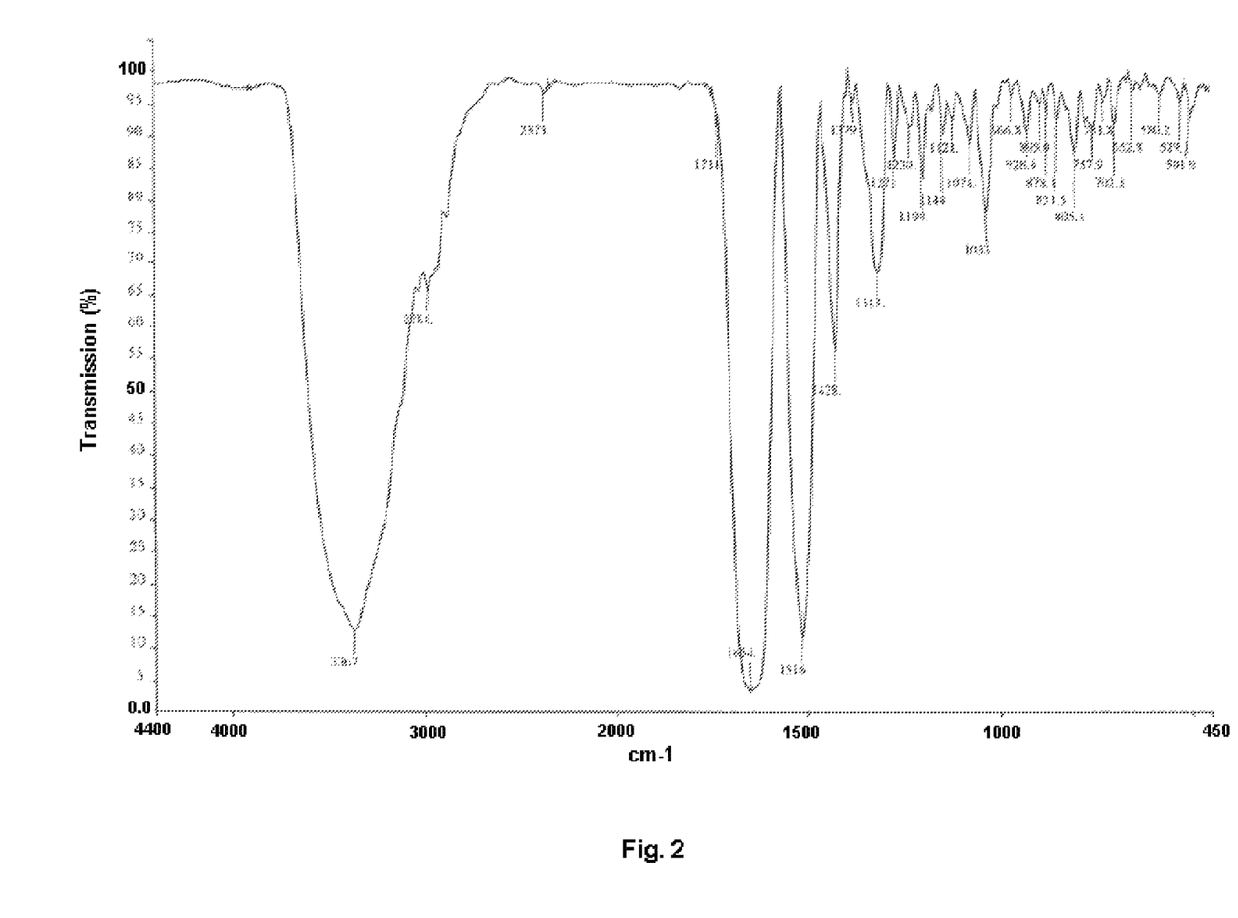
FIG. 2 shows the infrared absorption (IR) spectrum of PM181104.
Figure 3:
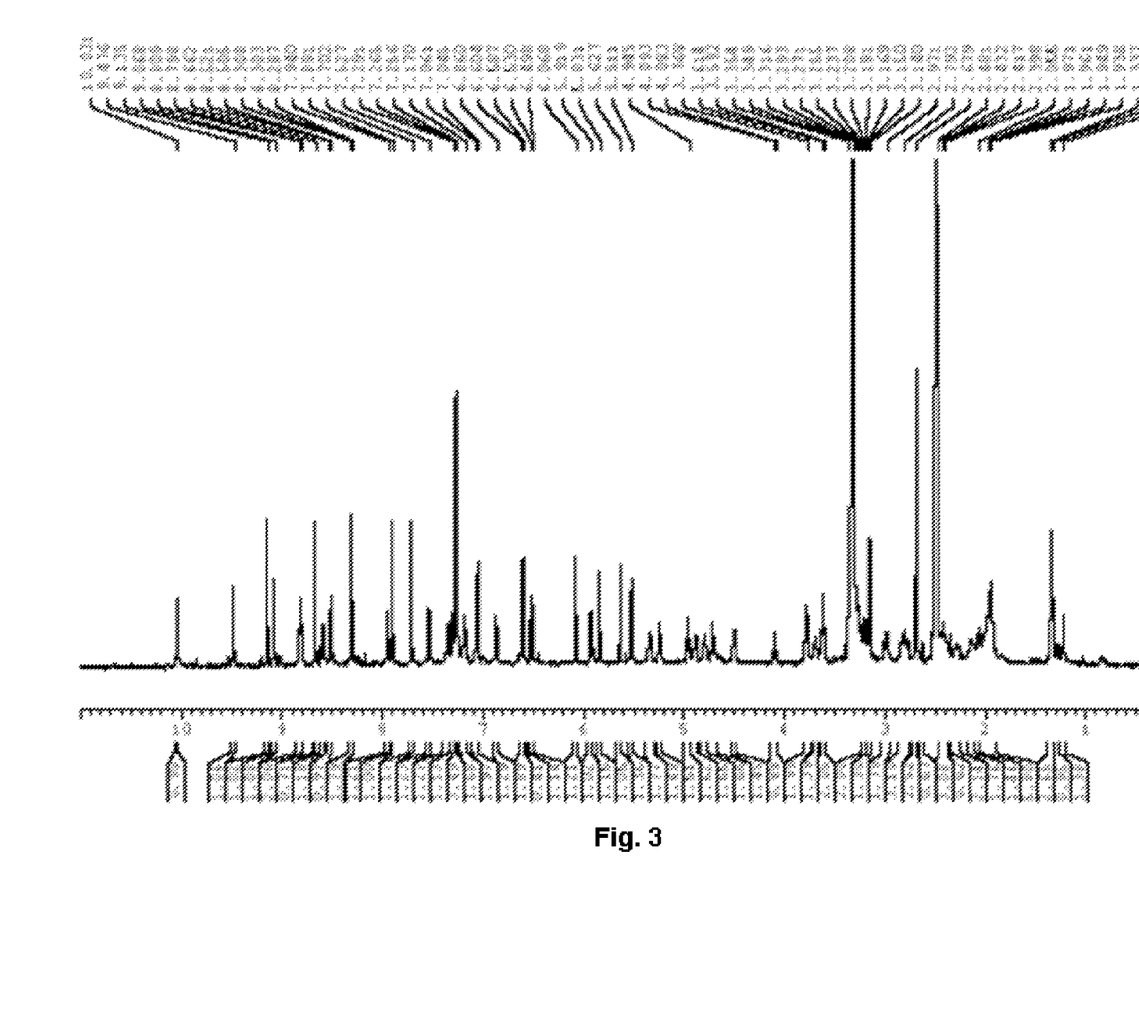
FIG. 3 shows the $^1$H-NMR spectrum (500 MHz) of PM181104 in DMSO-$d_6$.
Figure 4:
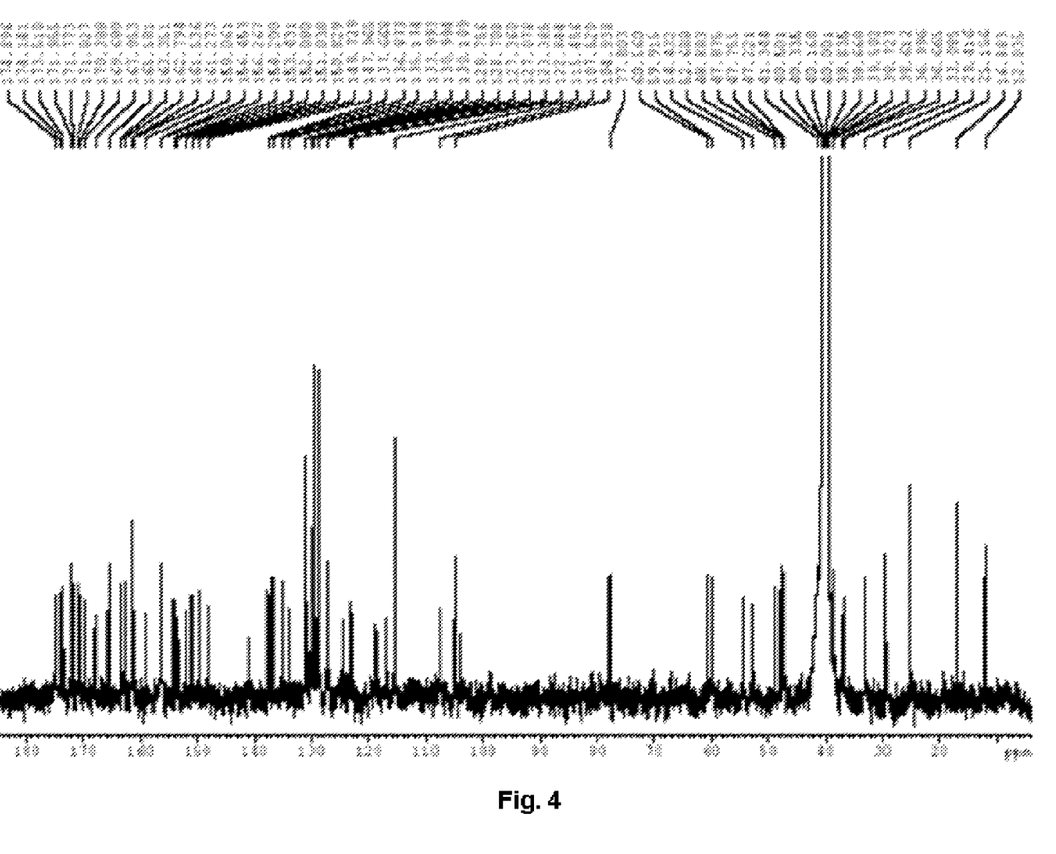
FIG. 4 shows the $^{13}$C-NMR spectrum (125 MHz) of PM181104 in DMSO-$d_6$.

3. The compound PM181104 as claimed in claim 2, wherein the compound PM 181104 has antibacterial activity, is isolated from the fermented broth of the microorganism belonging to *Kocuria* species (ZMA B-1/MTCC 5269) and is characterised by:

(a) the molecular weight of 1514, (b) the molecular formula $C_{69}H_{66}N_{18}O_{13}S_5$, (c) the UV spectrum as depicted in FIG. 1, (d) the IR spectrum as depicted in FIG. 2, (e) the $^1H$ NMR spectrum as depicted in FIG. 3, and (f) the $^{13}C$ NMR spectrum as depicted in FIG. 4.

4. A process for the production of the compound PM 181104 as claimed in claim 2, comprising the steps of:

(a) cultivating the microorganism *Kocuria* species (ZMA B-1/MTCC 5269) under submerged aerobic conditions in a nutrient medium containing sources of carbon and nitrogen to produce the compound PM 181104, (b) isolating the compound PM 181104 from the fermented broth, and (c) purifying the compound PM 181104.

5. A process as claimed in claim 4, further comprising the step of converting the compound PM 181104 to its pharmaceutically acceptable salt.

6. A process as claimed in claim 4, further comprising the step of reacting the compound PM181104 with an acid having the formula RCOOH; wherein R is alkyl, cycloalkyl, aryl or heterocyclyl, to obtain the novel compounds of formula I Formula I wherein is alkyl, cycloalkyl, aryl or heterocyclyl.

7. The compound as claimed in claim 1 wherein R is

CH₃CH₂CH₂CO, CH₃(CH₂)₁₅CH₂CO or

8. A pharmaceutical composition, comprising an effective amount of the compound as claimed in claim 1, with at least one pharmaceutically acceptable excipient or an additive or an auxiliary.

9. The pharmaceutical composition as claimed in claim 8, wherein the pharmaceutical composition is in the form of a tablet, coated tablet, capsule, granule, powder, cream, ointment, gel, emulsion, suspension, or solution for injection.

10. A pharmaceutical composition as claimed in claim 8, wherein said composition is adapted for the treatment of gram-positive bacterial infection.

11. The pharmaceutical composition as claimed in claim 10, wherein said bacterial infection is caused by bacteria belonging to *Staphylococcus, Streptococcus, Enterococcus* or *Bacillus* species.

12. The pharmaceutical composition as claimed in claim 11, wherein said bacteria belong to *Staphylococcus* or *Enterococci* species.

13. The pharmaceutical composition as claimed in claim 12, wherein said bacteria belonging to *Staphylococcus* species is methicillin-resistant.

14. The pharmaceutical composition as claimed in claim 12, wherein said bacteria belonging to *Staphylococcus* species is vancomycin-resistant.

15. The pharmaceutical composition as claimed in claim 12, wherein said bacteria belonging to *Enterococci* species is vancomycin-resistant.

16. A method of treating a bacterial infection comprising administering to a mammal in need thereof an effective amount of a compound as claimed in claim 1, wherein the bacterial infection is caused by a gram-positive bacteria.

17. The method as claimed in claim 16, wherein the bacterial infection is caused by bacteria belonging to *Staphylococcus, Streptococcus, Enterococci* and *Bacillus* species.

18. The method as claimed in claim 17, wherein the bacterial infection is caused by bacteria belonging to *Staphylococcus* or *Enterococci* species.

19. The method as claimed in claim 18, wherein said bacteria belonging to *Staphylococcus* species is methicillin-resistant.

20. The method as claimed in claim 18, wherein said bacteria belonging to *Staphylococcus* species is vancomycin-resistant.

21. The method as claimed in claim 18, wherein bacteria belonging to *Enterococci* species is vancomycin-resistant.

* * * * *